United States Patent [19]

Winterbotham et al.

[11] 4,144,201
[45] Mar. 13, 1979

[54] LIQUID DETERGENT COMPOSITIONS HAVING IMPROVED DRAIN-DRY AND MILDNESS PROPERTIES

[75] Inventors: Peter Winterbotham, Wirral; Jeffrey D. Hampson, Birkenhead, both of England

[73] Assignee: Lever Brothers Company, New York, N.Y.

[21] Appl. No.: 848,438

[22] Filed: Nov. 3, 1977

[30] Foreign Application Priority Data

Nov. 5, 1976 [GB] United Kingdom ............... 46193/76

[51] Int. Cl.$^2$ .......................... C11D 1/14; C11D 1/83
[52] U.S. Cl. .................................... 252/547; 252/545; 252/551; 252/DIG. 14; 252/DIG. 17
[58] Field of Search ............... 252/547, 551, DIG. 14, 252/526, 532

[56] References Cited

U.S. PATENT DOCUMENTS

| | | | |
|---|---|---|---|
| 3,739,233 | 2/1974 | Rose et al. | 252/547 |
| 3,775,349 | 11/1973 | Tuvell et al. | 252/547 |
| 3,898,186 | 8/1975 | Mermelstein et al. | 252/528 |
| 3,928,249 | 12/1975 | Nunziata et al. | 252/526 |
| 3,943,234 | 3/1976 | Roggenkamp | 424/343 |
| 3,956,199 | 5/1976 | Dawson et al. | 252/545 |
| 3,963,649 | 6/1976 | Spadini et al. | 252/546 |
| 4,070,309 | 1/1978 | Jacobsen | 252/547 |

FOREIGN PATENT DOCUMENTS

1082076   9/1967   United Kingdom.

OTHER PUBLICATIONS

The Condensed Chemical Dictionary, 4th Ed., Rheinhold Publishing Co., (1950), N. Y., pp. 145–146.

*Primary Examiner*—P.E. Willis, Jr.
*Attorney, Agent, or Firm*—Melvin H. Kurtz

[57] ABSTRACT

An improved cleaning composition, comprising an amine oxide, an alkylether sulphate, casein and optionally other nonionic detergent compounds and an organophosphorus compound. The composition, which is free from alkylbenzene sulphonates, alkyl sulphonates and alkyl sulphates, has improved drain-dry properties and improved mildness properties.

9 Claims, No Drawings

LIQUID DETERGENT COMPOSITIONS HAVING IMPROVED DRAIN-DRY AND MILDNESS PROPERTIES

The invention relates to a cleaning composition, and more particularly to a mild cleaning composition suitable for all sorts of applications where there is contact with the skin, such as in the manual dishwashing area, in hand and hair washing, and possibly also in the personal washing area. The invention is of particular advantage for use in manual dishwashing operations.

In manual dishwashing operations the objects to be cleaned are usually washed in a hand-warm aqueous solution of a suitable dishwashing composition, and subsequently put on a rack and dried with a tea-cloth. During the period between the cleaning and the cloth-drying some of the wash liquor may dry up on the objects and leave spots or streaky films. This can be reduced by rinsing the cleaned objects with running tap water or immersing them in a bowl with clean water, but the film of water on the objects left on the rack may not drain and dry evenly or quickly and the consequence thereof is that they may need to be polished or cloth-dried to prevent spotting. It has already been proposed to improve the "drainage" properties of dishwashing compositions by the inclusion of gelatin, which is said to allow a "sheeting-off" effect. Objects cleaned with such compositions may, after having been rinsed under running tap water, be left to stand and drain, thus obviating a cloth-drying operation.

The present invention now provides an improved liquid cleaning composition comprising casein, an amine oxide and an alkylether sulphate. The composition of the invention is free from alkylbenzene sulphonates, alkyl sulphonates and alkyl sulphates.

Hence the active detergent system used in the present invention in conjunction with casein, is free from alkylbenzene sulphonates, alkyl sulphonates and alkyl sulphates and consists essentially of an alkylether sulphate and a nonionic detergent component, selected from the group consisting of amine oxides, and mixtures of amine oxides and other nonionic detergent compounds.

It has been found that the composition of the invention shows improved "sheeting-off" properties and improved post-rinsing "drain-dry" properties, combined with real mildness properties to the skin.

The effect found is surprising since casein belongs to quite a different class of proteins than gelatin. Casein is a phosphoprotein whereas gelatin is a scleroprotein. Certainly the drain-dry effect is not a property that can be attributed to proteins in general. Experiments have shown that a number of protein types, such as egg-albumin, bovine albumin, $\beta$-lactoglobulin, pepsin, fibrinogen and various protein hydrolysates were found ineffective.

Also, apparently certain compatibility and concerted action rules between casein and the active detergent system must be satisfied in order to combine mildness effect with a good drain-dry effect and a good washing performance.

These conditions are fulfilled according to the invention by a composition which is free from alkylbenzene sulphonates, alkyl sulphonates and alkyl sulphates, and comprises casein in combination with an active detergent system consisting essentially of an alkylether sulphate and a nonionic detergent component, selected from the group consisting of amine oxides and mixtures of amine oxides and other nonionic detergent compounds.

The nonionic detergent compound which can be used in the present invention is generally the alkylene oxide condensation products of primary or secondary, straight or branched chain $C_8-C_{24}$ alcohols, $C_8-C_{18}$ alkyl or dialkyl phenols, $C_8-C_{24}$ fatty acid mono- and diamides, and glycols. In general these condensation products contain from 1–30, usually from 3–25 moles of ethylene oxide and/or propylene oxide.

Typical examples of suitable nonionics of the above group are primary $C_{12}-C_{15}$ alcohols condensed with 7–12 moles of ethylene oxide and secondary $C_{11}-C_{15}$ alcohols condensed with 9–12 moles of ethylene oxide.

A typical group of nonionic detergent compounds used in the present invention is amine oxides. Amine oxides are reaction products of tertiary amines and hydrogen peroxide or peroxyacids, having the general formula $R \, R_1 \, R_2 \, N \rightarrow O$, of which R may be aliphatic, aromatic, heterocyclic, alicyclic or combinations thereof. The amine oxides of interest in the present invention have R being a straight or branched chain aliphatic hydrocarbon radical having 8 to 20 carbon atoms, which may be saturated or unsaturated, and $R_1$ and $R_2$ being a methyl-, ethyl-, hydroxymethyl or a hydroxyethyl group.

Typical examples are dodecyldimethylamine oxide and the various fatty-acid-derived alkyl — $R_1 \, R_2$ — amine oxides, such as coconut dimethylamine oxide, lauryl dimethyl amine oxide and stearyl dimethyl amine oxide.

Mixtures of amine oxide and several of the above nonionic detergents can also be used.

The alkylether sulphates are salts of the monosulphuric acid esters of $C_8-C_{24}$ primary or secondary, straight or branched chain alcohols, which have been condensed with 1–18 moles of an alkylene oxide, e.g. ethylene oxide and/or propylene oxide. Particularly suitable are the $C_{12}-C_{18}$ primary alcohols condensed with from 2–10 moles of ethylene oxide, which have subsequently been sulphated and neutralized.

A typical example thereof is laurylether sulphate containing 3–5 moles of ethylene oxide; another typical example is a secondary $C_{11}-C_{15}$ alcohol condensed with 3–7 moles of ethylene oxide and subsequently sulphated and neutralized.

The salts of the alkylether sulphate are the alkali metal, ammonium, and substituted ammonium salts.

Casein is a known, commercially available, protein obtained from skim milk by acid or enzyme precipitation, reference to which can be found in Kirk-Othmer, Encyclopaedia of Chemical Technology 1949, Vol. 3, pages 225–237; and the Encyclopaedia of Polymer Science and Technology 1965, Interscience Publishers, Volume 2, pages 859–871. It has found commcercial use in various branches of industry.

The casein to be included in the cleaning composition of the invention can be $\alpha$, $\alpha_s$, $\beta$, $\gamma$, or whole casein, but for commercial reasons whole casein is preferred. Both acid casein and rennet casein can be used. It can be added as such, dissolved in a small amount of alkali, or as an aqueous solution of commercially available sodium caseinate. The amount of casein to be incorporated in the composition according to the invention is generally from about 0.25 to 5%, and preferably from about 1 to 3% by weight.

Accordingly the invention provides a cleaning composition comprising an amine oxide having the general formula R R$_1$ R$_2$ N→O, wherein R is a straight or branched chain aliphatic hydrocarbon radical, which may be saturated or unsaturated, having 8 to 20 carbon atoms and R$_1$ and R$_2$ are methyl, ethyl, hydroxy-methyl, or hydroxy-ethyl groups, a C$_8$-C$_{24}$ alkylether sulphate having 1-10 alkylene oxide groups, and 0.25-5.0% by weight of casein, and optionally other nonionic detergent compounds, which composition is free from alkylbenzene sulphonates, alkyl sulphonates and alkyl sulphates. The absence of said latter detergent active compounds is essential since they tend to adversely affect the mildness properties and also the drain-dry properties under soft water conditions.

Advantageously the total amount of nonionic detergent compound and alkylether sulphate present in the composition will be at least 10% by weight and may vary up to about 70% by weight of the total composition, the weight ratio between the nonionic detergent component and the alkylether sulphate being from 1:5 to 2:1, preferably from 1:4 to 1:1.

Within the above specified ratios the cleaning composition of the invention will contain about:

|  | general | preferably |
|---|---|---|
| total nonionic detergent compound | 5-35% | 7.5-30% |
| amine oxide | 2-35% | 5-30% |
| alkylether sulphate | 5-35% | 10-30% |
| casein | 0.25-5.0% | 1-3% |
| balance water. |  |  |

The composition of the invention may furthermore contain the usual ingredients, commonly incorporated in dishwashing or in skin and hair washing compositions. Such ingredients are hydrotropes, such as ethanol, urea, sodium xylene and toluene sulphonate, perfumes, colouring materials, opacifiers, preservatives and so on.

It has also been found that the further inclusion of an organophosphorus compound as defined hereafter in the composition of the invention gives an improved dishwashing composition in that it improves drain-drying whilst providing for an additional benefit in that the rinsability of these compositions is enhanced, thereby gaining the full benefit of the invention with less rinsing. The organophosphorus compound used here can be a phosphate ester or a phosphonate having the general formula R—(EO)$_n$—(O)$_m$—PO$_3$X$_2$, wherein R is a straight or branched chain alkyl having 8-18 carbon atoms, or a phenylalkyl-hydrocarbon chain wherein the alkyl group has 10-18 carbon atoms; (EO) is an ethylene oxide or propylene oxide group; n = 0-10; m = 0-1; and X is hydrogen or an alkali metal, ammonium or substituted ammonium cation. Particularly suitable phosphorus compounds are phosphate esters having the general formula R(EO)$_n$–OPO$_3$X$_2$, wherein R is a straight chain or branched chain hydrocarbon radical having 8-18 carbon atoms, preferably 11-15 carbon atoms; (EO) is an ethylene oxide or propylene oxide group; n is a number from 1-10, preferably 3-7; and X is hydrogen, or an alkali metal, ammonium or substituted ammonium cation. A typical example is the sodium salt of the monophosphoric acid ester of a C$_{11}$-C$_{15}$ alcohol, condensed with 3-5 moles of ethylene oxide. The amount of organophosphoric compound, when incorporated, is generally small, in the order of 0.5-5%, preferably 0.5-3.0% by weight of the total composition.

Accordingly, in one preferred embodiment of the invention the composition comprises an amine oxide, an alkylether sulphate, casein and an organo-phosphorus compound as defined above in an amount of about 0.5 to 5% by weight based on the total composition.

The compositions of the invention can be made up in the form of aqueous liquids or concentrated non-aqueous liquids. They are preferably, however, in the form of aqueous liquids.

As stated above, the compositions of the invention are particularly suitable for manual dishwashing operations, in which, after cleaning, the cleaned objects are rinsed with running tap water (either hot or cold), or by immersing them in a bowl with clean hot or cold water, and then left to stand to dry. The adhering film of water will rapidly drain or sheet off, and the objects will dry without showing significant spotting or streaking effects.

The invention will now be further illustrated by the following Examples.

Examples I-III

The following composition was tested and used at a concentration of 1.5 g/l in water of 40° FH. Plates were immersed in the wash liquor (at 40°-45° C.) for 30 seconds, then rinsed thoroughly in water of the same hardness and temperature under running tap water for 4 seconds. The composition showed good drain-dry effect with good overall end result scores.

| Composition | % by weight I |
|---|---|
| sodium lauryl-3 EO-sulphate | 24.0 |
| coconut dimethylamine oxide | 8.5 |
| C$_{11-15}$ sec. alcohol/12 ethylene oxide | 8.5 |
| urea | 9.0 |
| ethanol | 7.0 |
| sodium caseinate | 1.0 |
| water | to 100.0 |

Two other formulations of the invention were tested and found to show good drain-dry and rinsing properties. The percentages are by weight.

| Compositions | II | III |
|---|---|---|
| Sodium lauryl-3-ethylene oxide-sulphate | 24.0% | 32.5% |
| coconut dimethyl amine oxide | 8.5% | 8.5% |
| C$_{11-15}$ sec. alcohol/12-ethylene oxide | 8.5% | — |
| urea | 9.0% | 9.0% |
| ethanol | 7.0% | 7.0% |
| sodium caseinate | 1.0% | 1.0% |
| C$_{11-15}$-alkyl-(oxyethylene)$_3$-OPO$_3$Na$_2$ | 1.0% | 1.0% |
| water | to 100.0% | 100.0% |

For comparison the following compositions, containing gelatin instead of casein, were tested in the same manner:

| Composition (% by weight) | A | B | C | D |
|---|---|---|---|---|
| secondary C$_{12-16}$-alkyl sulphonate | 9.1 | 9.1 | — | — |
| sodium lauryl-(3-ethylene oxide) sulphate | 9.5 | 9.5 | 24.4 | 24.4 |
| lauryl dimethyl amine oxide | 3.8 | 3.8 | 5.6 | 5.6 |
| polyethylene glcyol 600 | 7.6 | 7.6 | — | — |

-continued

| Composition (% by weight) | A | B | C | D |
|---|---|---|---|---|
| gelatin (250 bloom-limed) | 1.5 | 1.5 | 1.5 | 1.5 |
| alcohol | 7.0 | 7.0 | 7.0 | 7.0 |
| $C_{11-15}$-alkyl-(oxyethylene)$_3$-OPO$_3$Na$_2$ | — | 1.2 | — | 1.2 |
| sodium xylene sulphonate | — | — | 3.8 | 3.8 |
| water | to 100.0 | 100.0 | 100.0 | 100.0 |

The post-rinsing drainage performance of products A and C were categorised as "slow to very slow drain-dry effect. Most of the plate remains hydrophilic".

The results with products B and D were: "Moderately fast to fairly fast slightly uneven drain-dry effect. Very extensive tail remains".

EXAMPLE IV

In this Example it is shown that composition (IV) of the invention has satisfactory drain-dry properties over a wider range of water-hardness degrees than the compositions outside the invention:

| Composition (% by weight) | E | F | IV |
|---|---|---|---|
| Na-secondary $C_{12-16}$-alkyl sulphonate | 32 | 20.5 | — |
| Na-$C_{12-15}$-alkyl-(3-ethylene oxide) sulphate | 8 | 12 | 32.5 |
| $C_{12-14}$-alkyl dimethyl amine oxide | — | 8.5 | 8.5 |
| casein | 1.5 | 1.5 | 1.5 |
| Water hardness above which consistent drain-dry was obtained | 36° | 24° | 12° |

The above results show that a departure from the composition of the invention reduces the drain-dry delivery.

EXAMPLE V

In clinical trials the skin condition of housewives was monitored over a four week period whilst using the test dishwashing formulations F and IV of Example IV and a formulation IV' without casein.

It was found that the panel of housewives using formulation IV have better hand condition than panels using formulations F and IV' (without casein). The rankings in terms of improvement in hand condition over the control standard formulations based on alkylbenzene sulphonate and an alkylethersulphate are:

IV > IV' > F.

We claim:

1. An aqueous liquid cleaning composition, which is free of alkyl benzene sulphonates, alkyl sulphonates and alkyl sulphates, and comprising:
   a. 5 to 35% by weight of said composition of a $C_8$-$C_{24}$ alkylether sulphate having 1 to 10 alkylene oxide groups,
   b. 5 to 35% by weight of said composition of a nonionic detergent active compound selected from the group consisting of amine oxides having the general formula $RR_1R_2N \rightarrow O$ wherein R is a straight or branched chain aliphatic hydrocarbon radical which may be saturated or unsaturated having 8 to 20 carbon atoms, and $R_1$ and $R_2$ are methyl, ethyl, hydroxymethyl or hydroxyethyl groups, and mixtures of said amine oxides and nonionic alkylene oxide condensation products.
   c. 0.25 to 5.0% by weight of soluble casein.

2. A liquid cleaning composition according to claim 1, wherein the weight ratio between said alkylethersulphate and said nonionic detergent active compound is from 5:1 to 1:2.

3. A liquid cleaning composition according to claim 2, wherein said ratio is from 4:1 to 1:1.

4. A liquid cleaning composition according to claim 1, which comprises 2 to 35% by weight of an amine oxide.

5. A liquid cleaning composition according to claim 1, wherein component (a) is present at a level of 10 to 30% by weight, component (b) is present at a level of 7.5 to 30% by weight of which at least 5% by weight is amine oxide, and component (c) is present at a level of 1 to 3% by weight.

6. A liquid cleaning composition according to claim 1, wherein said alkylether sulphate is derived from a primary $C_{12}$-$C_{18}$-alcohol condensed with 2-10 moles of ethylene oxide.

7. A liquid cleaning composition according to claim 1, which further comprises an organophosphorus compound having the general formula R—(EO)$_n$—(O)$_m$—PO$_3$X$_2$, wherein R is a straight or branched chain alkyl having 8-18 carbon atoms, or a phenylalkyl hydrocarbon chain wherein the alkyl group has 10-18 carbon atoms; (EO) is an ethylene oxide or propylene oxide group; n = 0-10; m = 0-1; and X is hydrogen or an alkali metal, ammonium or substituted ammonium cation, in an amount of about 0.5 to 5.0% by weight of the total composition.

8. A liquid cleaning composition according to claim 7, wherein said organophosphorus compound is a phosphate ester having the general formula R(EO)$_n$—OPO$_3$X$_2$, wherein R is a straight chain or branched chain hydrocarbon radical having 8-18 carbon atoms; (EO) is an ethylene oxide or propylene oxide group; n is a number from 0-10; and X is hydrogen, or an alkali-metal, ammonium or substituted ammonium cation.

9. A liquid cleaning composition according to claim 8, wherein said phosphate ester has R containing 11 to 15 carbon atoms; n is between 3 and 7 and X is a sodium cation.

* * * * *